Figure 1:
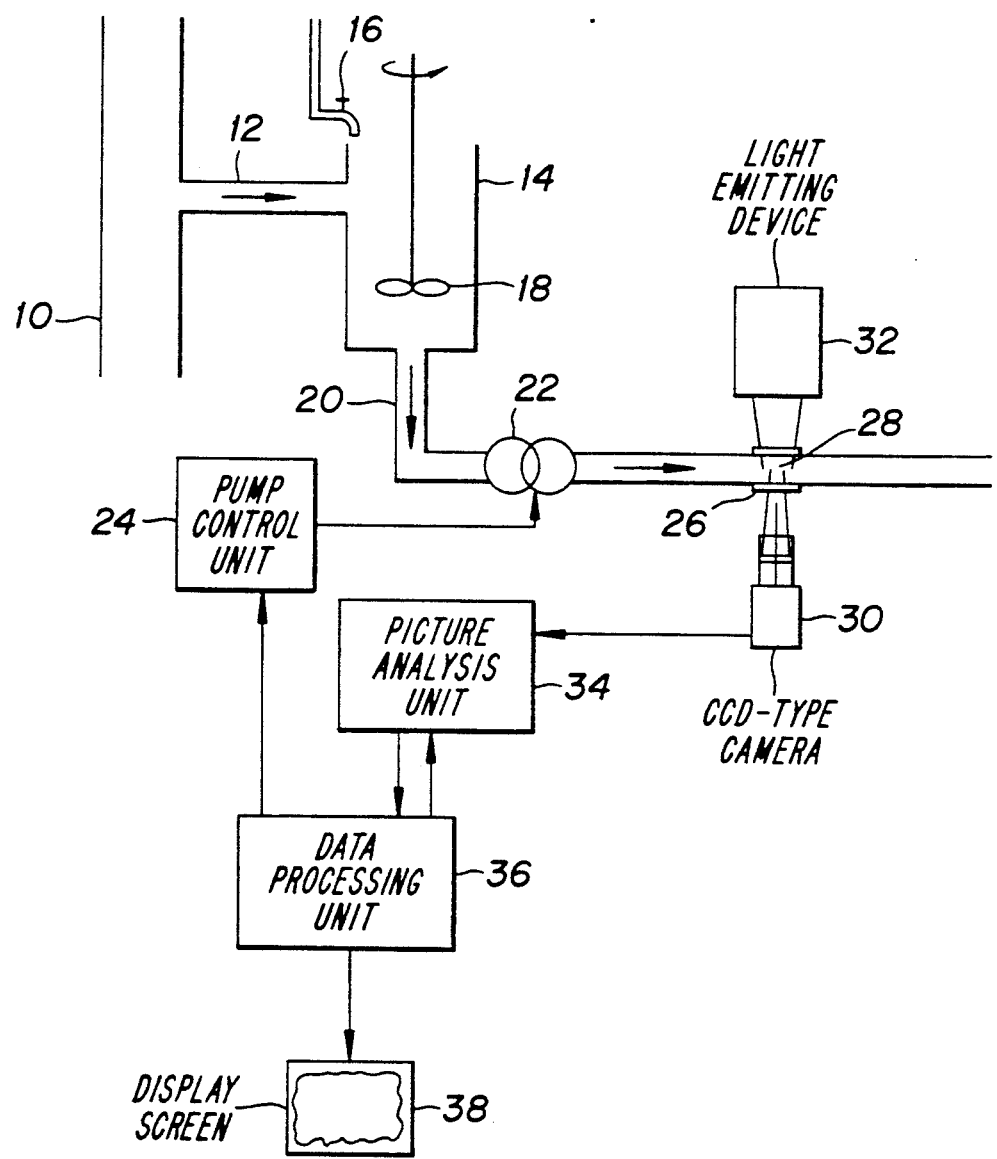

United States Patent [19]

Fransson et al.

[11] Patent Number: 5,331,405
[45] Date of Patent: Jul. 19, 1994

[54] METHOD AND APPARATUS FOR MEASURING FIBRE FLEXIBILITY

[75] Inventors: Per-Ivar Fransson; Hakan Karlsson, both of Akersberga; Lehard Kastre, Uppland Väsby, all of Sweden

[73] Assignee: STFI, Stockholm, Sweden

[21] Appl. No.: 859,293

[22] PCT Filed: Sep. 25, 1991

[86] PCT No.: PCT/SE91/00642
§ 371 Date: Jun. 24, 1992
§ 102(e) Date: Jun. 24, 1992

[87] PCT Pub. No.: WO92/05423
PCT Pub. Date: Apr. 2, 1992

[30] Foreign Application Priority Data

Sep. 26, 1990 [SE] Sweden .................. 9003056-0

[51] Int. Cl.⁵ .................................................. G01B 11/00
[52] U.S. Cl. ......................................... 356/372; 348/142
[58] Field of Search ............... 356/372, 373, 383, 384, 356/385; 358/107

[56] References Cited

U.S. PATENT DOCUMENTS 4,253,329 3/1981 Karnis ............................. 73/63

Primary Examiner—F. L. Evans
Attorney, Agent, or Firm—Burns, Doane, Swecker & Mathis

[57] ABSTRACT

A method for measuring the flexibility of fibers, particularly cellulose fibres, in a flowing suspension. The fibre form of a large number of fibres is registered at two different pictures of suspension flow. A predefined fibre form is calculated for each flow picture, and a relationship, for example the quotient between two measurements of mean fibre form is determined and utilized to define fibre flexibility. The invention also relates to an arrangement for carrying out the inventive method, wherein the arrangement includes a flow-through container (20) through which the suspension flows, a transparent window (26) mounted in the container wall, a CCD-type camera (30) which functions to photograph fibres passing the window, a picture analysis unit (34) coupled to the camera (30), and a data processing unit (36) for processing information obtained from the picture analysis unit (34).

17 Claims, 2 Drawing Sheets

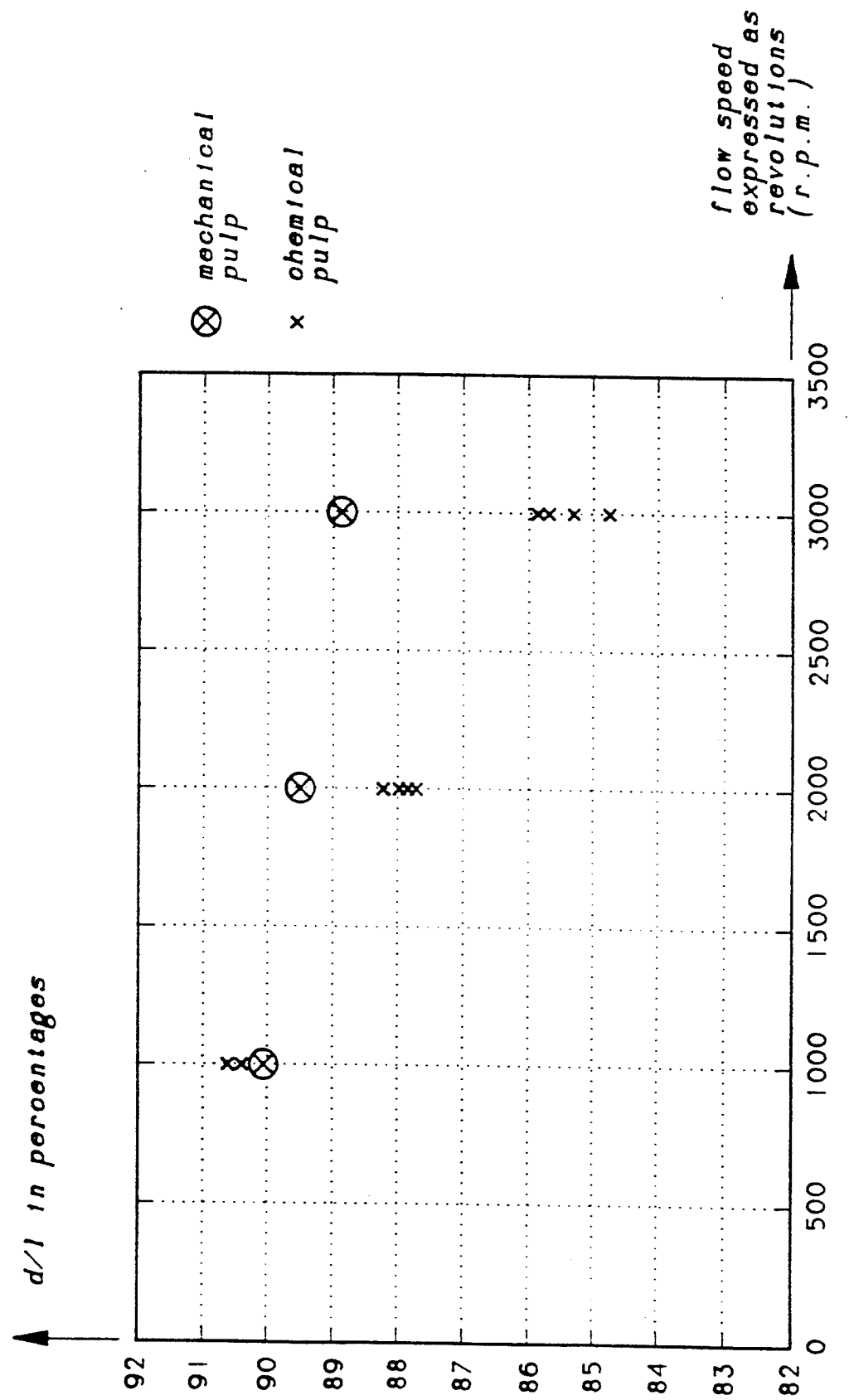

METHOD AND APPARATUS FOR MEASURING FIBRE FLEXIBILITY

The present invention relates to a method for measuring the flexibility of fibres, particularly cellulose fibres, in a flowing suspension. The invention also relates to an arrangement for measuring the flexibility of fibres in accordance with the novel method.

In order to be able to vary the quality of paper in paper manufacturing processes, it is important to know the various properties of the fibre material used in such processes. Paper of the type and quality desired can be produced by controlling the fibre properties of the fibres used. One of the properties of the fibre material used is the flexibility of the actual fibre itself. Various methods are known by means of which fibre flexibility can be measured. These known methods are based on measuring individual fibres or fibre samples which are disposed in a particular manner, subjected to load and the downward flexing or bending of the fibres, for example, is recorded.

One such measuring method is described in an article entitled "The Flexibility of Wet Pulp Fibres" by P.A. Tam Doo and R.J. Kerekes presented in the publication Pulp and Paper, Canada, 83:2 (1982), wherein a fibre support system is used for measuring individual fibres. The article also discloses the significance of measuring fibre flexibility.

An example of a laboratory method for measuring fibre flexibility is described in an article entitled "The Hydrodynamic Behaviour of Paper-Making Fibres" by O.L. Forgacs, A.A. Robertson and S.G. Mason presented in the publication Paper and Paper magazine of Canada, May 1958. In this case, fibres are classified in laminar flow in a shear field with respect to the rotational paths of the fibres, wherein several different rotational paths that are dependent on the flexibility of the fibres are described.

As before indicated, the aforedescribed, known methods are used solely for off-line-measuring purposes. The object of the present invention, however, is to enable the flexibility of fibres to be measured automatically, i.e. rapidly, such as to be enable fibre flexibility to be measured on-line. Naturally, the measuring process shall also be capable of being carried out in a simple fashion and of providing a definite measuring result.

According to the present invention, the fibre-flexibility measuring method described in the introduction is characterized primarily by registering the fibre form of a large number of fibres at two different suspension flow states, which are created, for example, by varying the rate of suspension flow within the framework of a given flow geometry, by calculating a predefined fibre form for each flow picture, and by determining a relationship, e.g. the quotient, between the two measurements of the predefined fibre form, i.e. the mean fibre form, and utilizing this relationship to define fibre flexibility. Advantageous embodiments of the novel measuring method are set forth in the following dependent method claims.

It will be noted that several different methods are known by means of which fibre form can be defined. In those measuring processes carried out in conjunction with the inventive method, the fibre form has been given as the relationship between actual or true fibre length and the length of the diagonal in a fixedly located rectangle which circumscribes the fibre. The orientation of the rectangle has therewith been locked and coupled to the equipment and not to the direction of the fibre. The fibre has also been assumed to be oriented in a two-dimensional plane.

The arrangement constructed for the purpose of carrying out the inventive method is particularly characterized in that it includes a tubular container for accommodating the flowing suspension; a transparent window provided in the container wall; a CCD-type camera which functions to photograph fibres flowing past the window; a picture analysis unit coupled to the camera; and a data processing unit for processing information delivered from the picture analysis unit.

Advantageous embodiments of the novel measuring arrangement are set forth in the following dependent apparatus claims.

The invention will now be described in more detail with reference to illustrative equipment for measuring fibre flexibility, wherein FIG. 1 is a schematic plan view of the novel measuring arrangement when used for measuring the flexibility of fibres in a fibre suspension obtained from a process line; and FIG. 2 illustrates the result of measuring the flexibility of cellulose fibres at different suspension flow rates.

Shown to the left in FIG. 1 is a process line 10 through which fibre suspension is conducted, while to the right of this line there is shown an illustrative example of a measuring arrangement constructed in accordance with the invention and functioning to carry out an on-line-measuring process. A shunt or branch conduit 12 connected to the process line 10 extends to a tank 14 in which the fibre suspension taken from the process line 10 is diluted to a desired consistency. Also shown in the drawing is a tap 16 from which diluting liquid is drawn. Mounted in the dilution tank 14 is a rotator 18, by means of which the diluted suspension is thoroughly mixed. The diluted suspension is passed from the dilution tank 14 to a conduit 20, through which the suspension is fed at the desired rate. The flow rate is regulated by means of a pump 22, which is controlled via a pump control unit 24. Mounted in the wall of the conduit 20 is a transparent window 26, which may include a cuvette, where the suspension is forced past a constriction 28 in the form of a gap whose one dimension is in the order of millimeters and whose other dimension, transversely to the flow direction, is greater than the maximum fibre length. Mounted adjacent the cuvette on one side of the conduit 20 is a CCD-type camera 30, while mounted on the other side of the conduit 20 is a light emitting device 32 which functions to illuminate the fibre suspension flowing through the cuvette.

The CCD-camera 30 delivers information in signal form to a picture analysis unit 34, for example of the type GOP 300, in which information received from the camera 30 is analyzed. The analysis carried out on each fibre photographed by the CCD-camera 30 is concerned with the perimeter of the fibre, i.e. its circumference, its area and its extension in-the X and Y directions. These last two parameters are used for calculating the length of the diagonal in the rectangle which circumscribes the fibre. The perimeter is used for length calculation. Since the length of a fibre is much greater than its width, the perimeter divided-by two (2) will provide a sufficiently accurate measurement of the length of the fibre. It is intended that the volume of the fibre can be estimated from the area of the fibre and its length and that this volume is then used as a weighting factor when making mean value calculations.

The picture analysis unit 34 has an electrically reciprocating coupling to a data processing unit 36, which is connected to a display screen 38 on which data is presented, and to the earlier mentioned pump control unit 24.

The diagramme shown in FIG. 2 illustrates measurements that have been obtained from fibres of mutually different flexibility. It will be seen from the diagramme that a chemical pulp, i.e. a digested pulp in which the fibres having been broken down chemically, is more flexible than a mechanical pulp, i.e. a pulp which has been degraded mechanically, which is well in agreement with known factual conditions. When carrying out the measuring processes, each measuring sequence included 10,000 fibres and the width of the measuring gap in the cuvette was 0.5 mm. The numerals along the X-axis of the diagramme state the rotational speed (r.p.m.) of the pump incorporated in the conduit 20 of the FIG. 1 embodiment. The rate of suspension flow through the conduit 20 is thus linearly proportional to this speed. The numerals along the Y-axis of the diagramme state the percentage units relating to the relationship between the aforesaid rectangle-diagonal d and the fibre length L. Thus, when bending of a fibre increases in response to an increased load, the diameter in the smallest describing rectangle decreases. Since the length of the fibre is unchanged, there is obtained a longer measurement for the fibre form (d/L) in accordance with said definition.

It will be understood that the described method and arrangement can be modified within the scope of the following claims. The method of producing different flow states can also be varied.

We claim:

1. A method for measuring the flexibility of fibres in a flowing suspension, comprising the steps of:
   recording a fibre form of a large number of fibres at two different suspension flow states;
   calculating, at each of the two different suspension flow states, a predefined fibre form for each of the different suspension flow states based on the recorded fibre forms;
   determining a relationship between the predefined fibre forms taken at the two different flow states; and
   utilizing this relationship to define fibre flexibility.

2. A method for measuring the flexibility of fibres according to claim 1, further comprising the step of recording a measurement of the fibre form of the flow states by photographing and subsequently analyzing more than 1,000 fibres.

3. A method for measuring the flexibility of fibres according to claim 1 or 2, further comprising the step of accelerating and/or retarding the flowing fibre suspension in an otherwise unchanged flow geometry such as to obtain different flow states.

4. A method for measuring the flexibility of fibres according to claim 1, further comprising the step of expressing the fibre form for each fibre as the relationship between the length of a diagonal (d) of a rectangle which circumscribes the fibre and a length (L) of said fibre.

5. A method according to claim 1, wherein the predefined fibre form is the mean fibre form.

6. A method for measuring the flexibility of fibres according to claim 1, wherein the fibres are cellulose fibres.

7. A method according to claim 6, wherein the two different suspension flow states are created by varying the rate of suspension flow within the framework of a given flow geometry.

8. A method according to claim 2, wherein 5,000–10,000 fibres are photographed and subsequently analyzed.

9. A method according to claim 1, wherein the two different states of suspension flow are at two different flow rates.

10. An arrangement for measuring the flexibility of fibres in a flowing suspension, wherein the fibre form of a large number of fibres is recorded at two different states of suspension flow, wherein a predefined fibre form is calculated for each flow state, and wherein a relationship between two measurements of the predefined fibre form is determined and used to define fibre flexibility, the arrangement comprising a flowthrough container for the flowing suspension, a transparent window in the container wall, a CCD-type camera for photographing fibres which pass the window, a picture analysis unit which is coupled to the camera, and a data processing unit for processing information delivered by the picture analysis unit.

11. An arrangement according to claim 10 for measuring the flexibility of fibres, wherein the data processing unit is programmed to calculate control and presentation data intended for controlling the flow of suspension through the container and for presentation on a presentation screen respectively.

12. An arrangement according to claim 10, further comprising a pump which functions to regulate the flow of suspension through the flowthrough container, wherein a pump control unit, which is electrically coupled to the data processing unit, controls the pump and therewith the rate of flow of the suspension through the flowthrough container.

13. An arrangement according to claim 10, wherein the container communicates with a process line (10) for fibre suspension.

14. An arrangement according to claim 13, further comprising a tank for diluting the fibre suspension taken from the process line positioned upstream of the container, as seen in the feed direction of the suspension.

15. An arrangement according to any one of claims 10 or 14, characterized in that the window in the flowthrough container includes a cuvette, adjacent which picture registration takes place; and in that a light-emitting source is mounted on the side of the cuvette opposite the camera, for illuminating the fibre suspension.

16. An arrangement according to claim 15, wherein the cuvette forms a gap in the container in the measuring direction; and in that the fibres are able to move freely in the two remaining directions.

17. An arrangement according to claim 10, for measuring the flexibility of fibres, wherein the fibres are cellulose fibers.

* * * * *